United States Patent [19]

Schulz et al.

[11] 4,235,728

[45] Nov. 25, 1980

[54] DRILLING FLUIDS CONTAINING NOVEL COMPOSITIONS OF MATTER

[75] Inventors: Johann G. D. Schulz, Pittsburgh; Jaroslav Zajac, Monroeville, both of Pa.

[73] Assignee: Gulf Research & Development Company, Pittsburgh, Pa.

[21] Appl. No.: 25,109

[22] Filed: Mar. 29, 1979

[51] Int. Cl.$^3$ .......................... C09K 7/02; C07C 51/41
[52] U.S. Cl. ............................. 252/8.5 C; 252/8.5 A; 252/8.5 P; 260/501.1; 562/410
[58] Field of Search .............. 252/8.5 A, 8.5 C, 8.5 P; 562/410

[56] References Cited

U.S. PATENT DOCUMENTS

| | | | |
|---|---|---|---|
| 2,545,169 | 3/1951 | Salathiel | 252/8.5 |
| 2,813,826 | 11/1957 | Crowley et al. | 252/8.5 |
| 3,468,943 | 9/1969 | Creighton et al. | 562/407 |
| 3,709,931 | 1/1973 | Proell et al. | 562/407 |
| 4,052,448 | 10/1977 | Schulz et al. | 521/143 X |
| 4,147,882 | 4/1979 | Schulz et al. | 562/410 |

OTHER PUBLICATIONS

Rogers, *Composition and Properties of Oil Well Drilling Fluids,* Third Edition, Pub. 1963, pp. 531, 544–546, 555.

*Primary Examiner*—Herbert B. Guynn

[57] ABSTRACT

A drilling fluid containing a new composition of matter resulting from the reaction of (1) substantially water-insoluble polycyclic, polycarboxylic acids obtained as a result of the oxidation of coal with (2) a base.

22 Claims, No Drawings

DRILLING FLUIDS CONTAINING NOVEL COMPOSITIONS OF MATTER

BACKGROUND OF THE INVENTION

1. Field of the Invention

This invention relates to (I) a drilling fluid containing a new composition of matter resulting from the reaction of (1) substantially water-insoluble polycyclic, polycarboxylic acids obtained as a result of the oxidation of coal with (2) a base and (II) said new composition of matter.

2. Description of the Prior Art

Rotary drilling is a technique that has been commonly used to drill a hole into the earth for the purpose of reaching a gas or oil formation. During this process a drilling fluid is passed downwardly through a rotating drill pipe and through the nozzles of a bit at its lower end, flowed upwardly in the annulus between said drill pipe and the borehole wall and then returned to the surface. The drilling fluid must possess (1) satisfactory viscosity and yield value to rapidly lift drilled formation cuttings to the surface, (2) the ability to plaster effectively the wall of the borehole to minimize drilling fluid leakage into the formation and (3) gel strength sufficient to permit effective suspension of drilled formation cuttings when drilling fluid circulation is interrupted or ceases. Since it is now common to reach formation depths wherein temperatures can be as high as about 150° C., and even higher, it is imperative that drilling fluids be heat stable in order to maintain their desired effectiveness.

A drilling fluid that has been extensively used for a long period of time contains water and a clay, such as bentonite, attapulgite or sepiolite. However, since these drilling fluids are deficient in one or more of the necessary properties enumerated above, it has been the custom to chemically treat such drilling fluids by incorporating therein specific additives to overcome specific deficiencies. Although the treatment of drilling fluids with one or more specific additives can improve some specific properties thereof, such additives can affect other properties of the drilling fluids, requiring the additional incorporation therein of still more additives. Through such development, however, complex mixtures of clay minerals with a large number of interacting chemicals have been produced. Therefore, it has become difficult economically to control the physical and chemical properties of clay-based drilling fluids.

Among the additives that have been suggested for incorporation in aqueous clay-based drilling fluids are the water-soluble alkali metal salts of carboxylated benzene or substituted alkyl benzene, wherein the benzene carries from three to six carboxyl groups, in U.S. Pat. No. 2,545,169 to Salathiel. Crowley et al, in U.S. Pat. No. 2,813,826, subjects a lignitic material to partial oxidation in an aqueous alkaline media, and can incorporate the total product, or the total liquid product, with or without some or all of the water removed therefrom or portions of the liquid product extractable with a strong mineral acid, a low-boiling ether or an alcohol or ketone, in an aqueous clay-based drilling fluid.

Instead of incorporating a large number of additives in an aqueous clay-based drilling fluid, it would be desirable to prepare a simpler drilling fluid containing little or no clay.

SUMMARY OF THE INVENTION

We have discovered unique compositions of matter resulting from the reaction of (1) a mixture of substantially water-insoluble polycyclic, polycarboxylic acids obtained as a result of the oxidation of coal with (2) a base. We have unexpectedly found that these new compositions can be added to water, fresh or salt water, and the resulting compositions obtained from these components are heat-stable drilling fluids possessing satisfactory range of plastic viscosity, yield value and gel strength, the ability to substantially reduce or minimize drilling fluid leakage in a formation and the additional ability to emulsify oil in the drilling fluid when, for example, an oil is present as a lubricant.

The substantially water-insoluble polycyclic, polycarboxylic acids employed in the reaction with a base herein can be obtained by any conventional or suitable procedure for the oxidation of coal. Bituminous and subbituminous coals, lignitic materials and other types of coal products are exemplary of coals that are suitable herein. Some of these coals in their raw state will contain relatively large amounts of water. These can be dried prior to use and preferably can be ground in a suitable attrition machine, such as a hammermill, to a size such that at least about 50 percent of the coal will pass through a 40-mesh (U.S. Series) sieve. The carbon and hydrogen content of the coal are believed to reside primarily in multi-ring aromatic and non-aromatic compounds (condensed and/or uncondensed), heterocyclic compounds, etc. On a moisture-free, ash-free basis the coal can have the following composition:

TABLE I

|  | Weight Percent | |
|---|---|---|
|  | Broad Range | Preferred Range |
| Carbon | 45–95 | 60–85 |
| Hydrogen | 2.2–8 | 5–7 |
| Oxygen | 2–46 | 8–40 |
| Nitrogen | 0.7–3 | 1–2 |
| Sulfur | 0.1–10 | 0.2–5 |

Any conventional or suitable oxidation procedure can be used to convert the coal to the desired substantially water-insoluble polycyclic, polycarboxylic acids. For example, a stirred aqueous slurry containing coal in particulate form, with or without a catalyst, such as cobalt, manganese, vanadium, or their compounds, can be subjected to a temperature of about 60° to about 225° C. and an oxygen pressure of about atmospheric (ambient) to about 2000 pounds per square inch gauge (about atmospheric to about 13.8 MPa) for about one to about 20 hours. The product so obtained can then be subjected to mechanical separation, for example filtration, and solid residue can be washed with water, if desired, and dried. The solid product remaining will be the desired mixture of substantially water-insoluble polycyclic, polycarboxylic acids, hereinafter referred to as "coal carboxylate". A preferred procedure for preparing the desired coal carboxylate involves subjecting a slurry containing coal in particulate form to oxidation with nitric acid. An exemplary procedure for so converting coal to coal carboxylate is disclosed, for example, in U.S. Pat. No. 4,052,448 to Schulz et al. Thus, a slurry containing coal can be subjected to reaction with aqueous nitric acid having a concentration of about one to about 90 percent, preferably about three to about 70 percent, at a temperature of about 15° to about 200° C., preferably about 25° to about 100° C., and a pressure of about atmospheric to about 2000 pounds per square inch gauge (about atmospheric to about 13.8 MPa), preferably about atmospheric to about 500 pounds per square inch gauge (about atmospheric to about 3.5 MPa), for about five minutes to about 15 hours, preferably about two to about six hours. The resulting product is then subjected to mechanical separation, for example filtration, and the solid residue can be washed with water, if desired, and dried to produce the desired coal carboxylate. Although the entire mixture of substantially water-insoluble polycyclic, polycarboxylic acids obtained in the oxidation of coal can be used in the reaction with the base herein, in an embodiment that portion of the mixture, non-extractable or extractable with an organic polar solvent, such as acetone or methylethylketone, can be used separately. In a preferred embodiment the oxidation reactions are so controlled that the coal carboxylate obtained for reaction with the base will contain from about 10 to about 95 weight percent, or even higher, preferably about 50 to about 95 weight percent, insoluble in an organic polar solvent, with the rest, obviously, being soluble in the polar solvent.

The individual components of the coal carboxylate are believed to be composed of condensed and/or non-condensed aromatic and non-aromatic rings, with an average number of such rings in the individual molecules ranging from about two to about 10, but generally from about three to about eight. On the average it is believed the number of carboxyl groups carried by the individual molecules will range from about four to about 10, generally from about six to about eight. The average molecular weight can range from about 600 to about 3000, but generally can be from about 1000 to about 3000 and the average neutral equivalent from about 200 to about 1000, generally from about 300 to about 800. A typical analysis of the coal carboxylates on a moisture-free and ash-free basis that will be reacted with the base herein is set forth below in Table II.

TABLE II

|  | Weight Percent | |
| --- | --- | --- |
|  | Broad Range | Preferred Range |
| Carbon | 48–75 | 53–69 |
| Hydrogen | 3–7 | 2.2–6 |
| Nitrogen | 1–4.9 | 2–3.9 |
| Oxygen | 20–40 | 26–37 |
| Sulfur | 0.1–1.0 | 0.1–0.8 |

Any base or basic salt, organic or inorganic, that can react with an acid can be used herein to react with the coal carboxylate. Thus, hydroxides of the elements of Group IA and Group IIA of the Periodic Table can be used. Of these we prefer to use potassium, sodium or calcium hydroxide. In addition ammonium hydroxide can also be used. Among the organic bases that can be used are aliphatic amines having from one to 12 carbon atoms, preferably from one to six carbon atoms, such as methylamine, ethylamine, ethanolamine and hexamethylenediamine, aromatic amines having from six to 60 carbon atoms, preferably from six to 30 carbon atoms, such as aniline and naphthalamine, aromatic structures carrying nitrogen as a ring constituent, such as pyridine and quinoline, etc. By "basic salt" we mean to include salts whose aqueous solutions exhibit a pH in the basic region, such as potassium carbonate, sodium metasilicate, calcium acetate, barium formate, etc.

The reaction between the coal carboxylate and the base is easily effected. The amounts of reactants are so correlated that the amount of base used is at least that amount stoichiometrically required to react with all, or a portion (for example, at least about 10 percent, preferably at least about 50 percent), of the carboxyl groups present in the coal carboxylate. This can be done, for example, by dispersing the coal carboxylate in an aqueous medium, such as water, noting the initial pH thereof, adding base thereto while stirring and continuing such addition while noting the pH of the resulting mixture. Such addition can be stopped anytime. In the preferred embodiment wherein a large portion or substantially all of the carboxyl groups are desirably reacted with the base, addition of base is continued until a stable pH reading is obtained. The reactions can be varied over a wide range, for example, using a temperature of about 5° to about 150° C., preferably about 15° to about 90° C., and a pressure of about atmospheric to about 75 pounds per square inch gauge (about atmospheric to about 0.5 MPa), preferably about atmospheric (about 0.1 MPa). The resulting product can then be subjected, for example, to a temperature of about 20° to about 200° C. under vacuum to about 100 pounds per square inch gauge (under vacuum to about 0.69 MPa) for the removal of water therefrom. However, if desired the water need not be removed from the total reaction product and the total reaction product, or after removal of a portion of the water therefrom, can be used to prepare a drilling fluid as taught herein. The solid product remaining is the novel reaction product of (1) a mixture of substantially water-insoluble polycyclic, polycarboxylic acids (coal carboxylate) and (2) a base.

We have found that the above reaction product can be added to water to form heat-stable drilling fluids possessing a broad range of satisfactory plastic viscosity, yield value and gel strength, the excellent ability to reduce or minimize drilling fluid leakage in a formation and the additional ability to emulsify oil in the drilling fluid when, for example, oils are present as lubricants. Therefore, the chemical treatment with thinners or dispersants, fluid loss additives and emulsifiers, usually employed in conventional clay-based drilling fluids are not required for a satisfactory performance for the drilling fluids claimed herein.

These drilling fluids are easily prepared. Thus they can be admixed with water using any suitable means, for example stirring, until the final drilling fluid contains from about one to about 25 weight percent, preferably about five to about 15 weight percent of the reaction product defined above. Although the drilling fluid can be prepared at any suitable temperature and pressure, for example, a temperature of about 5° to about 90° C. and atmospheric pressure over a period of about 12 to about 24 hours, it is preferred that they be prepared at ambient temperature and ambient pressure. If desired, additives that are often incorporated into drilling fluids for a particular purpose, for example, electrolytes, such as potassium chloride or sodium chloride to enhance the inhibitive property of the drilling fluid toward clay cuttings (for example, about one to about 30 weight percent of the drilling fluid), weighting agents, such as barite (for example, amounts sufficient to obtain a density in the drilling fluid upto about 2.16 grams/cm$^3$), oil lubricants (for example, about three to about 20 volume percent of the drilling fluid), pH adjustment compounds, such as sodium hydroxide, potassium hydroxide or calcium hydroxide, can also be added to the drilling fluid at the time of its preparation or at any time thereafter.

DESCRIPTION OF PREFERRED EMBODIMENTS

The following properties of a number of drilling fluids were determined by the standard procedures recommended by the American Petroleum Institute, API-RP-13B, 4th Edition, November, 1972: plastic viscosity, yield value (point), 10-second and 10-minute gel strength and fluid losses at elevated temperature of 93° C. and 149° C. and a pressure of 500 pounds per square inch gauge (3.5 MPa). Testing for fluid loss was carried out in the Baroid Filter Press No. 387, which has a filter area of 22.6 square centimeters. Since this is one-half of the API filtration area, all filtrate volumes were multiplied by two to correlate with API specifications.

Experience has shown that drilling fluids tend to deteriorate at increasing bottom hole temperatures during drilling. This thermal instability of drilling fluids, referred to as drilling or heat aging, was simulated in the laboratory by placing some of the drilling fluids in a pressure cell and rotating the latter in an oven for selected periods of time at a temperature of 149° C.

The data obtained were evaluated as follows. Required plastic viscosity values are a function of drilling fluid weights. We believe an effective aqueous drilling fluid having a weighting from about 1.01 to about 1.56 grams per cubic centimeters should have a plastic viscosity of about 3 to about 25 centipoises. The yield value relates to the flowing property of the drilling fluid effective to provide good lifting properties for cuttings at minimum viscosity; a satisfactory yield value will have a numeral value in relationship to the plastic viscosity falling within the range of about 1:1 to about 1:3, preferably about 1:1 to about 1:2. 10-second and 10-minute gel strengths of about one to about eight pounds per 100 square feet (about 48 to about 383 Pa), and about one to about 29 pounds per square feet (about 48 to about 1389 Pa), respectively, are satisfactory. To ensure effective fluid loss control while drilling, API values at 93° C. should be less than about 20 milliliters per 30 minutes and at 149° C. should be less than about 30 milliliters per 30 minutes after heat aging for 24 hours or more at 149° C.

A number of mixtures of substantially water-insoluble polycyclic, polycarboxylic acids (coal carboxylate) was prepared as follows. One of the coals used in these preparations was a North Dakota lignite analyzing as follows, on a moisture-free basis: 67.19 weight percent carbon, 3.85 weight percent hydrogen, 22.73 weight percent oxygen, 0.55 weight percent sulfur, 1.03 weight percent nitrogen and 4.65 weight percent metals. The ash was further analyzed and found to contain 43 weight percent oxygen, 7.8 weight percent sulfur, and the remainder metals. In one preparation a subbituminous Big Horn coal from Wyoming analyzing as follows, on a moisture-free basis, was used: 73.09 weight percent carbon, 4.35 weight percent hydrogen, 1.24 weight percent nitrogen, 17.42 weight percent oxygen, 0.85 weight percent sulfur and 3.05 weight percent metals.

Into a two-liter stirred autoclave containing a slurry composed of 800 grams of dried powdered lignite and 640 milliliters of water at 80° C. there was added 130 milliliters of 70 percent aqueous nitric acid over a period of 60 minutes. After the addition was complete the mixture was maintained in the autoclave for an additional 240 minutes. During the entire period of time the temperature was maintained at 80° C. and atmospheric pressure (ambient pressure). At the end of the reaction, the resulting reaction mixture was subjected to filtration and the resulting solids were dried in a vacuum oven to obtain a mixture of substantially water-insoluble polycyclic, polycarboxylic acids. To determine the amount of polar solvent soluble material present in such mixture, the same was subjected to extraction with methylethylketone (MEK). Two additional similar runs were made. The data obtained are set forth below in Table III.

TABLE III

| Run No. | Coal, Grams | Slurry Water, Grams | Nitric Acid, Milliliters | Temperature, °C. | Addition Time, Minutes | Holding Time, Minutes | Coal Carboxylate Obtained | MEK Soluble in Coal Carboxylate Weight Percent |
|---|---|---|---|---|---|---|---|---|
| I | 800 | 640 | 130 | 80 | 60 | 240 | A | 7 |
| II | 800 | 640 | 195 | 80 | 85 | 210 | B | 8 |
| III | 800 | 640 | 260 | 80 | 120 | 180 | C | 10 |

Into a five-gallon stirred autoclave there was charged 3000 grams of water and 890 milliliters of 70 percent aqueous nitric acid. The mixture was heated to 80° C. at atmospheric pressure. To this mixture there was added a slurry containing 1500 grams of powdered North Dakota lignite and 1500 grams of water over a period of 30 minutes. There was then added to the autoclave 445 milliliters of 70 percent aqueous nitric acid at a rate of 20 milliliters per minute. An additional 3000 grams of slurry containing lignite and water, similar to the above, was added to the autoclave over a period of 30 minutes. The autoclave was held at 80° C. for a period of four hours from the initial addition of slurry thereto. The contents of the autoclave were cooled to ambient temperature, filtered and the resulting solids, composed of a mixture of substantially water-insoluble polycyclic, polycarboxylic acids (coal carboxylates), were dried as before and analyzed for their MEK-soluble content. The product obtained is identified in Table IV as Coal Carboxylate D. Two additional runs were carried out to prepare Coal Carboxylates E and F similar to the above except that the batches of coal slurry were added to the autoclave in twenty-minute periods and the coal carboxylates obtained were not dried. In preparing Coal Carboxylate E and total holding time was two hours instead of four. An additional Coal Carboxylate G was prepared as follows: Into a one-gallon stirred glass autoclave there was charged 320 milliliters of water and 100 milliliters of 70 percent aqueous nitric acid. The mixture was heated to 80° C. at ambient pressure. Concurrently there were added two streams over a period of 180 minutes: one containing 800 grams of the subbituminous coal defined above and a second composed of a mixture of 640 milliliters of water and 100 milliliters of 70 percent aqueous nitric acid. After addition was complete the contents of the autoclave were held at 80° C. for an additional 60 minutes. The reaction mixture was filtered and the solid product remaining, a mixture of substantially water-insoluble polycyclic, polycarboxylic acids (coal carboxylate), was dried in a vacuum oven and was found to contain 16.0 weight percent acids soluble in methylethyl ketone. The results of the above runs are summarized below in Table IV.

TABLE IV

| Run No. | Coal, Grams | Total Water, Grams | Total Nitric Acid, Grams | Temperature, °C. | Coal Addition Time, Minutes | Total Reaction Time, Minutes | Coal Carboxylate Obtained | MEK Solubles In Coal Carboxylate, Weight Percent |
|---|---|---|---|---|---|---|---|---|
| IV | 3000 | 6000 | 1335 | 80 | 60 | 240 | D | 25.5 |
| V | 3000 | 6000 | 1335 | 80 | 40 | 120 | E | 37.1 |
| VI | 3000 | 6000 | 1335 | 80 | 40 | 240 | F | 15.6 |
| VII | 800 | 960 | 200 | 80 | 180 | 240 | G | 16.0 |

EXAMPLE I

Drilling fluids were prepared as follows. 165 grams of Coal Carboxylate Mixture B were added to 44.9 grams of potassium hydroxide dissolved in 800 milliliters of distilled water and the mixture was mixed in a Waring blender. When gelling became apparent, the sample was transferred to a high-pressure shearing device (sonolator) and diluted with hard water (containing 300 parts per million of calcium ions and 20 parts per million of magnesium ions) to 1650 milliliters. The sonolator is used to simulate the effect of high pressure on shear degradation of the coal oxidate mixture. Since water used in preparing drilling is usually a hard water containing calcium and magnesium ions, a simulated hard water was used in the dilution. The resulting suspension was sheared in the sonolator for 40 minutes at 700 pounds per square inch gauge (4.8 MPa). 420 milliliters of the above suspension was diluted with an additional 280 milliliters of hard water to obtain a drilling fluid containing six weight percent of the reaction product of the coal carboxylate and potassium hydroxide. The concentration of calcium and magnesium ions in the drilling fluid was about 200 parts per million and 13 parts per million, respectively. The resulting drilling fluid had a pH of 9.7. This drilling fluid was then tested for its plastic viscosity, yield value, gel strength and fluid loss. To the drilling fluid so tested there was then added three weight percent potassium chloride to check the effect of electrolytes thereon. After the drilling fluid was again tested, it was aged at 149° C. for 24 hours and again tested.

EXAMPLE II

A drilling fluid was prepared following the procedure of Example I except that the mixture used in reaction with potassium hydroxide contained Coal Carboxylate A and Coal Carboxylate C. The drilling fluid tested also contained potassium chloride and was aged at 149° C. for 24 hours. Testing for fluid loss was carried out at 149° C.

EXAMPLE III

The drilling fluid prepared and tested herein following the procedure of Example II except that the mixture used in reaction with potassium hydroxide contained Coal Carboxylate A and Coal Carboxylate B.

EXAMPLE IV

The drilling fluid prepared herein followed the procedure of Example II except that the mixture used in the reaction with potassium hydroxide contained Coal Carboxylate D and was not sonolated. The sample was tested at 149° C. for 24 hours. After testing the sample was aged for an additional 64 hours at 149° C. and again tested. Thus the total time of aging for the latter sample was 88 hours.

The data obtained are tabulated below in Table V.

TABLE V

| Example | Aging at 149° C., Hours | Reaction Product, Weight Percent, (Coal Carboxylate) Mixture Used | KCl, Weight Percent | Plastic Viscosity, cp | Yield Value Pounds/100 Sq.Ft. (Pa) | Fann Gels 10 Sec. Pounds/100 Sq. Ft. (Pa) | Fann Gels 10 Min. (Pa) | pH | HT-HP API Fluid Loss at 500 PSI (3.5 MPa) 93° C. Ml/ 30 Min. | HT-HP API Fluid Loss at 500 PSI (3.5 MPa) 149° C. Ml/ 30 Min. |
|---|---|---|---|---|---|---|---|---|---|---|
| I A | — | 6.0 (B) | — | 4 | 4(192) | 1(48) | 1(48) | 9.7 | 17 | — |
| I B | — | 6.0 (B) | 3 | 11 | 13(622) | 6(287) | 16(766) | 9.8 | 14 | — |
| I C | 24 | 6.0 (B) | 3 | 10 | 8(383) | 8(383) | 9(431) | 8.5 | — | 19 |
| II | 24 | 7.0 (2.6 Percent from A) (4.4 Percent from C) | 3 | 13 | 5(239) | 3(144) | 5(239) | 9.3 | — | 29 |
| III | 24 | 7.0 (2.6 Percent from A) (4.4 Percent from B) | 3 | 10 | 11(527) | 8(383) | 12(575) | 9.1 | — | 19 |
| IV A | 24 | 8.0 (D) | 3 | 17 | 12(575) | 4(192) | 10(479) | 8.6 | — | 15 |

TABLE V-continued

| Example | Aging at 149° C., Hours | Reaction Product, Weight Percent, (Coal Carboxylate) Mixture Used | KCl, Weight Percent | Plastic Viscosity, cp | Yield Value Pounds/100 Sq.Ft. (Pa) | Fann Gels 10 Sec. Pounds/100 Sq. Ft. (Pa) | Fann Gels 10 Min. Pounds/100 Sq. Ft. (Pa) | pH | HT-HP API Fluid Loss at 500 PSI (3.5 MPa) 93° C. Ml/30 Min. | HT-HP API Fluid Loss at 500 PSI (3.5 MPa) 149° C. Ml/30 Min. |
|---|---|---|---|---|---|---|---|---|---|---|
| IV B | 88 | 8.0 (D) | 3 | 13 | 12(575) | 4(192) | 8(383) | 8.5 | — | 23 |

The data in Table V clearly show that excellent aqueous drilling fluids are prepared using the novel reaction product resulting from the reaction of coal carboxylates obtained as a result of the oxidation of coal with a base. The plastic viscosity of 4 cp in the basic drilling fluid of Example I indicates that it is satisfactory for a non-weighted drilling fluid. Since in many cases drilling fluids are prepared using sea water or contain alkali chlorides to inhibit shale hydration, it is interesting to note that the presence of potassium chloride in the drilling fluid of Example IB improves the desired qualities of the same. Since the viscosities and yield values and their ratios are excellent, this drilling fluid can be weighted, for example with barite, if desired. The reduction in fluid loss at 93° C. is remarkable and indicates that if an aggregated structure was responsible for the viscosity increase the filtration properties were not adversely affected thereby. The results obtained in Example IC indicate that the drilling fluids claimed herein are thermally stable and do not undergo the thermal degradation typical of many drilling fluids treated with organic polymeric colloids. Thus, the rheological properties of the drilling fluids remain almost unchanged; a slight decrease in yield value makes the gel-forming tendency less time dependent. The fluid loss determined at 149° C. is excellent and is a direct measure of the thermal stability of the reaction product of the coal acids with a base.

Since the performance of a drilling fluid is enhanced if the same is thermally stable, testing of heat-aged samples is needed for the ultimate evaluation of a drilling fluid formulation. Therefore the remaining tests in Table V were all made on aged drilling fluid samples. The data obtained in Examples II, III and IV show that even though the composition of the coal carboxylates used herein is varied, as evidenced by the varying content of the methyl ethyl ketone-solubles therein, and the process for obtaining such acid mixture is also varied, the drilling fluids prepared using the reaction product of coal carboxylates with a base are excellent. These data further indicate that following the dictates herein a drilling fluid can be tailored to fit the desired requirements in a particular drilling environment.

An additional series of runs was carried out wherein the effect of diesel oil addition and pH adjustment in the drilling fluids claimed herein was determined. These runs were carried out following the procedure of Example II using selected mixtures of substantially water-insoluble polycyclic, polycarboxylic acids. Diesel oil was incorporated in a selected number of drilling fluids. The pH of the drilling fluid was varied by the addition thereof of potassium hydroxide. The data obtained are tabulated below in Table VI.

TABLE VI

| Example | Aging at 149° C., Hours | Reaction Product, Weight Percent (Coal Carboxylate Used) | KCl, Weight Percent | Diesel Oil In Drilling Fluid, Volume Percent | Plastic Viscosity cp | Yield Value Pounds/100 Sq. Ft. (Pa) | Fann Gels 10 Sec. Pounds/100 Sq. Ft. (Pa) | Fann Gels 10 Min. Pounds/100 Sq. Ft. (Pa) | pH | HT-HP API Fluid Loss at 500 PSI (3.5 MPa) 93° C. Ml/30 Min. | HT-HP API Fluid Loss at 500 PSI (3.5 MPa) 149° C. Ml/30 Min. |
|---|---|---|---|---|---|---|---|---|---|---|---|
| V A | 64 | 8.0 (E) | 3.0 | — | 13 | 9(431) | 4(192) | 11(527) | 9.0 | — | 23 |
| V B | 64 | 8.0 (E) | 2.7 | 10 | 18 | 24(1149) | 13(622) | 30(1436) | 7.5 | — | — |
| V C | 64 | 8.0 (E) | 2.7 | 10 | 15 | 15(718) | 5(239) | 18(862) | 9.5 | — | 16 |
| VI A | 64 | 8.0 (F) | 3.0 | — | 17 | 16(766) | 6(287) | 23(1101) | 9.1 | — | 20 |
| VI B | 24 | 7.3 (F) | 2.7 | 10 | 20 | 21(1005) | 7(335) | 26(1245) | 8.8 | — | 14 |
| VII A | — | 7.0 (G) | 3.0 | 10 | 12 | 9(431) | 3(144) | 5(239) | 8.3 | 13 | — |
| VII B | 24 | 8.0 (G) | 3.0 | 10 | 14 | 5(239) | 3(144) | 5(239) | 8.2 | — | 28 |

The incorporation of an oil in a drilling fluid is not conceived as a chemical treatment. Since the oil is a lubricant, its primary functions are for the purpose of reducing the amount of torque on the drill pipe, to lengthen the bit-bearing life and to decrease the amount of wear in drilling fluid pumps. The purpose of the above runs was to determine the effect of a lubricant on the drilling fluid claimed herein. The rheological and fluid loss properties of the drilling fluid of Example VA are good. The addition of diesel oil to the drilling fluid in Example VB improved the plastic viscosity and yield values of the drilling fluid, but the gel strength values were marginal. However, as Example VC shows, increasing the pH of the drilling fluid from 7.5 to 9.5 resulted in a drilling fluid having excellent rheological properties and low fluid loss values. Examples VIA and VIB show that although the concentrations of the reaction product of coal acids with potassium hydroxide is reduced by the addition of the diesel oil thereto, the emulsified oil improves the rheological and filtration characteristics of the resulting drilling fluid. Moreover, the data show that the emulsion is stable at 149° C. after 24 hours of heat aging. This is remarkable considering that no emulsifier was added to the drilling fluid. It is apparent, therefore, that the presence of the defined novel reaction products in the drilling fluid performs three functions: they help to control the viscosity and the filtration properties of the drilling fluid and emulsify the oil. While in Example VB the diesel oil was incorporated in the initial stages of drilling fluid formulation, it was admixtured in the sample of Example VIB after heat aging for 64 hours at 149° C. in order to simulate drilling fluid maintenance during drilling aging. The data show that the emulsifying capability of coal carboxylates was not lost after 64 hours of heat aging, and an improvement of the rheological and filtration characteristics is apparent even after additional 24-hour aging. Considering the excellent ratio of plastic viscosity to yield value this drilling fluid could be weighted with barite to a density of 1.56 grams/cm$^3$. Examples VII A and B indicate that feeds used can be extended to coals other than lignite. The flowing and static properties and filtration characteristics of drilling fluids formulated with coal carboxylates derived from subbituminous coals are satisfactory and comparable in their performances to the drilling fluids prepared using carboxylates derived from lignite.

The application of clay-water drilling fluids poses a variety of problems connected with flow behavior, gelling and filtration characteristics, particularly in the presence of electrolytes and at increased temperatures. Since numerous and pertinent studies merely present data which emphasize the successful empirical approaches sufficient to remedy a specific problem, there is no good general and concise description of the basic clay-water behavior relevant for drilling fluid application that could be referred to for comparison. Accordingly, comparative tests were made with clay-water suspensions comparable to those prepared hereinabove.

EXAMPLE VIII

Bentonite suspensions were prepared by prehydrating 49.7 grams of bentonite in 280 milliliters of distilled fresh water overnight, after which the slurries were diluted with hard water to a total of 830 milliliters. To some of these suspensions there was added 24.9 grams of potassium chloride. The suspensions so prepared were sheared for one hour in a Waring blender. Additional suspensions were similarly prepared using 44.4 grams of attapulgite or sepiolite prehydrated in 162 milliliters of distilled water overnight. The slurries were diluted to 740 milliliters with hard water and 22.2 grams of potassium chloride were dissolved therein. These slurries were similarly sheared for one hour in a Waring blender. Each of the suspensions so prepared was tested with the results indicated in Table VII.

them as drilling fluids. Such chemicals include inorganic salts or organic compounds. However, chemical treatment can serve to retard, rather than to eliminate, the viscosifying and gelling of treated drilling fluids in use. This is because the chemicals used can undergo a thermal and shear degradation.

The data in Table VII also show that heat aging is synergestic with the electrolytic effect and substantiallydestroys the rheological and/or filtration properties of the drilling fluid. It appears that bentonite and sepiolite undergo hydrothermal breakdown and their suspensions are thereby converted into worthless gels, which then require treatment with thinners. However, thinners have a detrimental effect on mud rheology because of their ability to disperse drilled shale and clay cuttings and thereby incorporate them into the drilling fluid. Because of this the total amount of colloidal clay solids in the drilling fluid is increased, its viscosity rises, and the drilling fluid must be diluted and weighted to only retard the subsequent gelling cycle. Thus, in many cases clay-based drilling fluids must be treated with protective colloids or polymers which beneficiate the bentonite while drilling through shale formations. The needle-like particles of attapulgite form a deflocculated structure after heat aging. Since the swelling and hydration of attapulgite are low, its suspension, on one hand, must be treated with one additive to improve the rheology and, on the other hand, with an additive of polymeric nature to reduce the fluid loss. Although sepiolite-based drilling fluids are recommended for drilling in deep holes, the data indicate that its suspensions have the deficiencies typical of both bentonite and attapulgite suspensions and therefore require a heavy chemical treatment. A comparison of the data in Table VII with that of the drilling fluids claimed herein, as exemplified, for example, in Table VI, clearly shows the technical and commercial superiority of the drilling fluids claimed herein since they do not require chemical treatment for the same specified conditions.

The following exemplifies the deficiencies of an aqueous drilling fluid containing lignite.

EXAMPLE IX

The lignite used herein is a North Dakota lignite analyzing as follows, on a moisture-free basis: 67.19 weight percent carbon, 3.85 weight percent hydrogen, 22.73 weight percent oxygen, 0.55 weight percent sul-

TABLE VII

| Example | Aging at 149° C., Hours | Bentonite, Weight Percent | Attapulgite, Weight Percent | Sepiolite, Weight Percent | KCl, Weight Percent | Plastic Viscosity, cp | Yield Value Pounds/ 100 Sq. Ft. (Pa) | Fann Gels 10 Sec. Pounds/100 Sq. Ft. (Pa) | Fann Gels 10 Min. Pounds/100 Sq. Ft. (Pa) | pH | HT-HP API Fluid Loss at 500 PSI (3.5 MPa) 93° C. Ml/ 30 Min. | HT-HP API Fluid Loss at 500 PSI (3.5 MPa) 149° C. Ml/ 30 Min. |
|---|---|---|---|---|---|---|---|---|---|---|---|---|
| VIII A | — | 6.0 | — | — | — | 8 | 5(239) | — | 2(96) | 9.4 | 32 | — |
| VIII B | — | 6.0 | — | — | 3.0 | 36 | 69(3304) | 69(3304) | 73(3495) | 9.0 | 55 | — |
| VIII C | 65 | 6.0 | — | — | — | 48 | 72(3447) | 10(479) | 10(479) | 9.1 | — | 46 |
| VIII D | 65 | 6.0 | — | — | 3.0 | 18 | 232(11108) | 94(4501) | 108(5171) | 9.2 | — | 129 |
| VIII E | — | — | 6.0 | — | 3.0 | 6 | 43(2059) | 25(1197) | 25(1197) | 9.2 | * | — |
| VIII F | 65 | — | 6.0 | — | 3.0 | 6 | 13(622) | 9(431) | 10(479) | 8.8 | — | * |
| VIII G | — | — | — | 6.0 | 3.0 | 11 | 119(5698) | 53(2538) | 57(2729) | 9.2 | 192 | — |
| VIII H | — | — | — | 6.0 | 3.0 | 6 | 55(2633) | 49(2346) | 51(2442) | 9.2 | — | * |

*Denotes no shut off; that is, a thick, permeable cake formed which would not provide resistance to flow of filtrate into a formation.

The data in Table VII describing the behavior of the clay suspensions indicate that the electrolyte adversely affects the rheology and the filtration characteristics of these suspensions. Therefore it would appear imperative to treat chemically these suspensions prior to using fur, 1.03 weight percent nitrogen and 4.65 weight percent metals. The ash was further analyzed and found to contain 43 weight percent oxygen, 7.8 weight percent sulfur and the remainder metals. 248 grams of ground dry lignite were treated with 44.9 grams of potassium hydroxide dissolved in 800 milliliters of water and mixed in a Waring blender for 30 minutes, after which mixing was discontinued and the resulting suspension kept at rest overnight. The sample was transferred to a high pressure shearing device (sonolator), diluted with hard water to 3100 milliliters and sheared for 20 minutes at 700 pounds per square inch gauge (4.8 MPa). 1300 milliliters of an eight weight percent lignite suspension was sampled for testing. Another portion was diluted with 600 milliliters of hard water to 2400 milliliters, sheared and 1300 milliliters of a six weight percent lignite suspension was sampled for testing. The remainder was diluted with 550 milliliters sheared and 1300 milliliters of a four weight percent lignite suspension was sampled for testing. Some samples contained three weight percent potassium chloride. The rheology of each of the suspensions was determined, after which the samples were aged for 24 hours at 149° C. The samples for fluid loss testing were set aside for six days at ambient temperature. During this period, the aged samples separated in two phases, with the lignite settling in the lower phase. However, all the samples were thoroughly mixed prior to fluid loss testing. The data are tabulated below in Table VIII.

TABLE VIII

| Example | Aging at 149° C., Hours | North Dakota Lignite, Weight Percent | KCl, Weight Percent | Plastic Viscosity, cp | Yield Value Pounds/ 100 Sq. Ft. (Pa) | Fann Gels 10 Sec. | Fann Gels 10 Min. | pH | HT-HP API Fluid Loss at 500 PSI (3.5 MPa) 93° C. Ml/ 30 Min. | HT-HP API Fluid Loss at 500 PSI (3.5 MPa) 149° C. Ml/ 30 Min. |
|---|---|---|---|---|---|---|---|---|---|---|
| | | | | | | Pounds/100 Sq. Ft. (Pa) | | | | |
| IX A | — | 8.0 | — | 5 | 4(192) | 4(192) | 5(239) | 8.9 | 34 | — |
| IX B | — | 8.0 | 3.0 | 4 | 4(192) | 4(192) | 5(239) | 8.5 | 160 | — |
| IX C | 24 | 8.0 | 3.0 | 2 | 1(48) | 1(48) | 2(96) | 8.5 | — | 400 |
| IX D | — | 6.0 | — | 3 | 3(144) | 2(96) | 4(192) | 8.6 | 46 | — |
| IX E | — | 6.0 | 3.0 | 2 | 3(144) | 3(144) | 3(144) | 8.5 | 182 | — |
| IX F | 24 | 6.0 | 3.0 | 2 | 1(48) | 1(48) | 1(48) | 8.5 | — | 396 |
| IX G | — | 4.0 | — | 2 | 1(48) | 1(48) | 1(48) | 8.5 | 50 | — |
| IX H | — | 4.0 | 3.0 | 2 | 1(48) | 1(48) | 1(48) | 8.5 | — | * |

*Denotes no shut off.

The data in Table VIII amply show that suspensions prepared with lignite possess poor rheological properties and unacceptably high fluid loss characteristics, particularly in the presence of electrolyte and/or when they have been subjected to heat aging. Thus, it is not possible to formulate a simple lignite (coal) based drilling fluid.

EXAMPLE X

We have found that the novel drilling fluids claimed herein possess the following rheological properties which are significant for efficient drilling: necessary time-dependent thixotropic behavior and shear thinning behavior. A mixture containing 50 volume percent of each of the drilling fluids used in Examples IB and IC were subjected to evaluation in a Haake-Roto Viscometer. The shear stress-shear rate data of the uprun were measured on the fluid continuously broken until the point of highest shear rate. Immediately after the completion of the uprun, the shear stresses of the downrun were determined at the descending shear rates. The time interval to break down the structure in the uprun and to stabilize the structure in the downrun was three minutes. The data obtained in the uprun and downrun cycles are set forth below in Table IX.

TABLE IX

| Uprun | |
|---|---|
| Shear Rate, Sec.$^{-1}$ | Shear Stress, Dyne/Cm$^2$ |
| 1.1 | 7.7 |
| 2.2 | 9.9 |
| 5.4 | 16 |
| 11 | 19 |
| 22 | 21 |
| 43 | 25 |
| 86 | 29 |
| 173 | 36 |
| 345 | 44 |
| 689 | 53 |
| 976 | — |

| Downrun | |
|---|---|
| Shear Rate, Sec.$^{-1}$ | Shear Stress, Dyne/Cm$^2$ |
| 689 | 49 |
| 345 | 32 |
| 173 | 22 |
| 86 | 15 |
| 43 | 11 |
| 22 | 9 |
| 11 | 7 |
| 5.4 | 5.9 |
| 2.2 | 4.5 |
| 1.1 | 4.3 |

| Shear Rate, Sec.$^{-1}$ | Apparent Viscosity, cp |
|---|---|
| 173 | 21 |
| 345 | 13 |
| 689 | 8 |

The difference between the shear stresses of the uprun and the downrun illustrates the structure/shear relationship referred to as a thixotropic loop. The apparent viscosity computed for the shear rate range of the annular and drill pipe flow shows a considerable thinning from 21 cp to 8 cp. Extrapolating these values to a shear rate range of $10^5$ sec$^{-1}$ in a bit nozzle, the drilling fluid will thus provide a water-thin consistency of a few centipoises and thereby improve the drilling rate.

EXAMPLE XI

If a drilling fluid is inhibited and substantially non-dispersed, it minimizes osmotic hydration and suppresses shale clay swelling in borehole walls and in shale cuttings. This will appreciably suppress distintegration of shale cuttings and shale sloughing when drilling in shale formation. A qualitative evaluation of the inhibitive and non-dispersive characteristics was made by placing Upper Cody shale cuttings containing from 50 to 60 weight percent montmorillonite in (1) tap ater, (2) a three percent aqueous potassium chloride solution, (3) a drilling fluid, such as that of Example VB, and (4) the filtrate obtained from previous tests of said reaction products. The shale cuttings disintegrated in water within a few minutes, in the three weight percent potassium chloride solution within 24 hours, but no apparent change in the size of the cuttings in the drilling fluid and in the filtrate was found after three weeks. The cuttings were dried and were found to be encapsulated by a dark red film of the reaction product of the coal acid mixture and base.

In addition to the advantages, disclosed and illustrated above, possessed by our novel drilling fluids, the novel reaction product present therein can be crosslinked by hydrogen bonding in the presence of hydrated cations of amphoteric elements, such as zinc, aluminum, iron and chromium, to form a three-dimensional complex including the novel reaction product and such cations. The resulting compounds can also be used in drilling fluids to enhance the rheological properties and stability. If it becomes desirable to reduce the concentratration of the coal carboxylates or to enhance the viscosifying effects at a given concentration of the coal carboxylates in a drilling fluid, a small addition of heat-stable polymeric additives, such as polysacharides (biopolymers) can also be incorporated in the drilling fluid.

Obviously, many modifications and variations of the invention, as hereinabove set forth, can be made without departing from the spirit and scope thereof and, therefore, only such limitations should be imposed as are indicated in the appended claims.

We claim:

1. An aqueous clay-free drilling fluid containing water and from about one to about 25 weight percent of a new composition of matter resulting from the reaction of (1) substantially water-insoluble polycyclic, polycarboxylic acids obtained as a result of the nitric acid oxidation of coal, said oxidation comprising subjecting a slurry containing coal to reaction with aqueous nitric acid having a concentration of about one to about 90 percent at a temperature of about 15° to about 200° C. for about five minutes to about 15 hours, with (2) a base, said base being a hydroxide of an element of Group IA of the Periodic Table or a hydroxide of an element of Group IIA of the Periodic Table, a basic salt of an element of Group IA or IIA of the Periodic Table whose aqueous solutions exhibit a pH in the basic region, or ammonium hydroxide, the amount of said base, said basic salt or ammonium hydroxide, being at last an amount stoichiometrically required to react with at least about 50 percent of the carboxyl groups in said acids, the reaction between said acids and said base, said basic salt or ammonium hydroxide being in the range of about 5° to about 150° C.

2. The drilling fluid of claim 1 wherein said drilling fluid contains water from about five to about 15 percent of said new composition of matter.

3. The drilling fluid of claim 1 wherein said substantially water-insoluble polycyclic, polycarboxylic acids are obtained as a result of the nitric acid oxidation of coal, said oxidation comprising subjecting a slurry containing coal to reaction with aqueous nitric acid having a concentration of about three to about 70 percent at a temperature of about 50° to about 100° C. for about two to about six hours.

4. The drilling fluid of claim 1 wherein said coal subjected to oxidation is lignite.

5. The drilling fluid of claim 1 wherein said coal subjected to oxidation is a subbituminous coal.

6. The drilling fluid of of claim 1 wherein said coal subjected to oxidation is a bituminous coal.

7. The drilling fluid of claim 1 wherein said acids are reacted with a base, said base being a hydroxide of an element of Group IA of the Periodic Table.

8. The drilling fluid of claim 1 wherein said acids are reacted with a base, said base being a hydroxide of an element of Group IIA of the Periodic Table.

9. The drilling fluid of claim 1 wherein said acids are reacted with a base, said base being sodium hydroxide.

10. The drilling fluid of claim 1 wherein said acids are reacted with a base, said base being potassium hydroxide.

11. The drilling fluid of claim 1 wherein said acids are reacted with a base, said base being calcium hydroxide.

12. The drilling fluid of claim 1 wherein said reaction with said base, said basic salt or ammonium hydroxide is carried out at a temperature of about 15° to aout 90° C.

13. The drilling fluid of claim 1 wherein an oil lubricant is also present and emulsified in the water.

14. The drilling fluid of claim 1 wherein a diesel oil is also present and is emulsified in the water.

15. The drilling fluid of claim 1 wherein said acids are reacted with a basic salt of an element of Group IA of the Periodic Table whose aqueous solutions exhibit a pH in the basic region.

16. The drilling fluid of claim 1 wherein said acids are reacted with a basic salt of an element of Group IIA of the Periodic Table whose aqueous solutions exhibit a pH in the basic region.

17. The drilling fluid of claim 1 wherein said acids are reacted with potassium carbonate.

18. The drilling fluid of claim 1 wherein said acids are reacted with sodium metasilicate.

19. The drilling fluid of claim 1 wherein aid acids are reacted with calcium acetate.

20. The drilling fluid of claim 1 wherein said acids are reacted with barium formate.

21. The drilling fluid of claim 1 wherein said acids are reacted with ammonium hydroxide.

22. The drilling fluid of claim 1 wherein the amount of said base, said basic salt or ammonium hydroxide is an amount stoichiometrically required to react with all of the carboxyl groups in said acids.

* * * * *